(12) United States Patent
Gildersleeve

(10) Patent No.: US 9,986,772 B2
(45) Date of Patent: Jun. 5, 2018

(54) DISPOSABLE PADDED TAPE

(71) Applicant: DJO, LLC, Vista, CA (US)

(72) Inventor: Richard Gildersleeve, Carlsbad, CA (US)

(73) Assignee: DJO, LLC, Vista, CA (US)

( * ) Notice: Subject to any disclaimer, the term of this patent is extended or adjusted under 35 U.S.C. 154(b) by 0 days. days.

(21) Appl. No.: 14/484,202

(22) Filed: Sep. 11, 2014

(65) Prior Publication Data

US 2015/0075697 A1 Mar. 19, 2015

Related U.S. Application Data

(60) Provisional application No. 61/877,397, filed on Sep. 13, 2013.

(51) Int. Cl.

| *A41D 13/015* | (2006.01) |
|---|---|
| *A61F 17/00* | (2006.01) |
| *A61F 13/00* | (2006.01) |
| *A61F 13/02* | (2006.01) |
| *B32B 5/18* | (2006.01) |
| *B32B 7/14* | (2006.01) |
| *A41D 31/00* | (2006.01) |
| *A41D 13/00* | (2006.01) |
| *A41D 13/05* | (2006.01) |

(52) U.S. Cl.
CPC ...... *A41D 13/015* (2013.01); *A61F 13/00038* (2013.01); *A61F 13/023* (2013.01); *A61F 13/0253* (2013.01); *A61F 13/0256* (2013.01); *A61F 13/0273* (2013.01); *A61F 17/00* (2013.01); *B32B 5/18* (2013.01); *B32B 7/14* (2013.01); *A41D 13/0015* (2013.01); *A41D 13/05* (2013.01); *A41D 31/0044* (2013.01); *A61F 2013/00272* (2013.01); *B32B 2266/025* (2013.01); *B32B 2266/0221* (2013.01); *B32B 2307/56* (2013.01); *B32B 2535/00* (2013.01); *Y10T 156/10* (2015.01); *Y10T 428/24851* (2015.01)

(58) Field of Classification Search
None
See application file for complete search history.

(56) References Cited

U.S. PATENT DOCUMENTS

| D100,536 S | 7/1936 | Beniston | |
|---|---|---|---|
| 3,404,406 A | 10/1968 | Balliet | |
| 3,457,919 A | 7/1969 | Harbard et al. | |
| 3,581,883 A * | 6/1971 | Whitney | B65D 81/03 206/523 |
| 3,775,526 A | 11/1973 | Gilmore | |
| 4,505,976 A * | 3/1985 | Doehnert | A61L 24/043 428/355 AC |
| 4,733,659 A | 3/1988 | Edenbaum et al. | |
| 4,740,416 A | 4/1988 | Decoste, Jr. et al. | |
| 4,926,503 A | 5/1990 | Wingo, Jr. | |
| 5,055,340 A | 10/1991 | Matsumura et al. | |
| 5,203,764 A * | 4/1993 | Libbey | A43B 7/28 602/5 |
| 5,244,677 A * | 9/1993 | Kreckel | A61K 9/703 424/447 |
| 5,560,569 A | 10/1996 | Schmidt | |
| 5,718,245 A * | 2/1998 | Horn | A61F 15/001 128/897 |
| 5,732,412 A * | 3/1998 | Holden | A41D 13/065 2/23 |
| 5,915,819 A | 6/1999 | Gooding | |
| 6,016,915 A * | 1/2000 | Almond | A61F 15/001 206/441 |
| 6,035,452 A * | 3/2000 | Braxton | A41D 13/015 2/16 |
| D453,880 S | 2/2002 | Cheynet | |
| 6,453,477 B1 | 9/2002 | Bainbridge et al. | |
| 6,519,781 B1 | 2/2003 | Berns | |
| 6,673,029 B1 | 1/2004 | Watson | |
| 6,743,325 B1 | 6/2004 | Taylor | |
| D497,437 S | 10/2004 | Poliacek et al. | |
| 6,969,548 B1 * | 11/2005 | Goldfine | A41D 31/0061 206/523 |
| 7,100,216 B2 * | 9/2006 | Matechen | A41D 13/0156 2/455 |
| 7,208,216 B2 | 4/2007 | Ackerman et al. | |
| D609,922 S | 2/2010 | Bridges et al. | |
| 7,748,056 B2 | 7/2010 | Mickle | |

(Continued)

FOREIGN PATENT DOCUMENTS

| DE | 19640263 A1 | 4/1998 | |
|---|---|---|---|
| EP | 1290956 A2 * | 3/2003 | ......... A41D 13/0153 |
| EP | 1290956 A2 | 12/2003 | |
| FR | 2815519 A3 | 4/2002 | |
| GB | 2300808 B | 11/1996 | |
| GB | 2376170 A | 11/2002 | |
| GB | 2444915 B | 9/2011 | |
| WO | 2013024300 A1 | 2/2013 | |

OTHER PUBLICATIONS

Definition of "surface" from Merriam-Webster dictionary, retrived on Mar. 20, 2016.*
Istvan Benedek et al., "Pressure-Sensitive Adhesives Technology", 1997, Marcel Dekker Inc., Chapter 7, pp. 262, 288.*
"Introducing Defender Tape Customize Your Protection", DJO Global, 2015.*
McDavid, Padded athletic Garments, HEX/PADS, http://www.mcdavidusa.com/category/86_1/Default.aspx.
Mueller, Golfer's Grip Tape, Lightweight, Conforming Elastic Protective Tape, sold by MFASCO Health & Safety co., http://www.amazon.com/health-personal-care/dp/B000U0D4TE.

*Primary Examiner* — Anish Desai
(74) *Attorney, Agent, or Firm* — Veros Legal Solutions LLP

(57) ABSTRACT

Disclosed herein are devices for preventing or treating an injury to an individual. Also provided are devices and methods for alleviating pain or discomfort caused by equipment or other padding or articles of clothing or uniform. The device can include a disposable padded tape having a plurality of force absorbing zones. It can also include an adhesive layer for attaching the device to a body contacting surface.

7 Claims, 10 Drawing Sheets

(56) References Cited

U.S. PATENT DOCUMENTS

| | | |
|---|---|---|
| D626,718 S | 11/2010 | Turner |
| D626,719 S | 11/2010 | Turner |
| D627,135 S | 11/2010 | Turner |
| D628,769 S | 12/2010 | Turner |
| D629,999 S | 1/2011 | Turner |
| D633,688 S | 3/2011 | Turner |
| 7,992,226 B2 | 8/2011 | Turner |
| D648,439 S | 11/2011 | Greener et al. |
| 8,095,996 B2 | 1/2012 | Turner |
| 8,220,072 B2 | 7/2012 | Dodd |
| 8,281,414 B2 | 10/2012 | Mickle |
| 8,298,648 B2 | 10/2012 | Turner |
| 8,679,047 B2 | 3/2014 | Holt et al. |
| D708,751 S | 7/2014 | Chan et al. |
| 8,764,931 B2 | 7/2014 | Turner |
| 8,808,489 B2 | 8/2014 | Taylor |
| D726,326 S | 4/2015 | Schrammel |
| D745,688 S | 12/2015 | Chan et al. |
| D745,689 S | 12/2015 | Chan et al. |
| D745,690 S | 12/2015 | Devenish et al. |
| D748,344 S | 1/2016 | Snyder et al. |
| 9,358,256 B2 | 6/2016 | Devenish et al. |
| 2002/0138030 A1* | 9/2002 | Cavanagh ............ A61F 13/063 602/41 |
| 2004/0213979 A1 | 10/2004 | Vito et al. |
| 2004/0224151 A1* | 11/2004 | Horacek ................ A63B 49/08 428/354 |
| 2005/0081277 A1* | 4/2005 | Matechen .......... A41D 13/0156 2/102 |
| 2005/0193365 A1 | 9/2005 | Sahr |
| 2005/0228331 A1 | 10/2005 | Tseng et al. |
| 2006/0059609 A1 | 3/2006 | Moss |
| 2006/0199456 A1 | 9/2006 | Taylor |
| 2007/0276304 A1 | 11/2007 | Greenber et al. |
| 2008/0113143 A1* | 5/2008 | Taylor ................ A41D 31/005 428/47 |
| 2009/0270827 A1* | 10/2009 | Gundersen .............. A61F 13/02 604/369 |
| 2011/0098620 A1 | 4/2011 | Dever |
| 2011/0225847 A1 | 9/2011 | Buchanan |
| 2012/0132355 A1 | 5/2012 | Turner |
| 2012/0136328 A1 | 5/2012 | Johannison et al. |
| 2012/0141750 A1 | 6/2012 | Taylor |
| 2012/0232448 A1 | 9/2012 | Wust |
| 2014/0079900 A1 | 3/2014 | Ramirez |
| 2014/0143927 A1 | 5/2014 | Holt et al. |
| 2015/0375220 A1 | 12/2015 | Lukas et al. |

* cited by examiner

DISPOSABLE PADDED TAPE

CROSS-REFERENCE TO RELATED APPLICATIONS

This application claims priority to U.S. Provisional Patent Application Ser. No. 61/877,397, filed on Sep. 13, 2013, the entire contents of which is hereby incorporated by reference in its entirety.

BACKGROUND OF THE INVENTION

Field of the Invention

Disclosed herein is a disposable padded tape for use as protective padding. Methods of making and using the disposable tape to protect against injury are likewise described.

Description of the Related Technology

Protective wear is used as a barrier to absorb and dissipate energy that has the potential to cause injury to an individual. Protective wear is utilized, for example, in a range of sporting and leisure activities and within the building trade. Conventional protective wear may form an integral part of an item of clothing, for example a shoulder pad, or may be provided separately, for example a shin pad. Such arrangements are not versatile, as they are structured to protect a specific body part. It is therefore often necessary to purchase different protective wear for use in the protection of different parts of the body. Additionally, because conventional protective wear is purchased "off-the shelf", it is only available in a limited range of sizes or designs, and as such may not provide optimal protection for a specific user's body-part.

There is a need in the art for a more user-friendly protective padding which can be tailored for use on different body parts.

SUMMARY

Disclosed herein are devices and methods for use in the prevention or treatment of an injury to an individual. The devices and methods can also be used to alleviate pain or discomfort caused by equipment or other padding or articles of clothing, footwear, or uniform. They can be used for aesthetic reasons, for comfort, fit, and reduction of chafing. The devices can be applied to the skin and/or on top of or under other padding, tape, equipment, clothing, or any other surface where beneficial. It is contemplated that the devices and methods described herein are used in the sports industry but also have uses in any instance in which a protective barrier, cushion or padding would benefit the wearer.

According to an aspect, there is provided disposable tape for use in protecting against injury. The disposable tape may be configured as a sheet of tape or the tape can be wound convolutely in overlapping relationship upon itself to form a roll of disposable tape. In another aspect there are individual shapes and sizes of disposable tape that are individually packaged in a box, for example, such as Band-Aid® bandages (shapes could be simple rectangles or ovals, or optimized to fit specific body parts/joints like the knee, shin, elbow, nose etc.) configured for application to a body surface or other surface for the prevention or treatment of an injury to an individual.

The tape comprises a first layer having a bottom and top surface, wherein the bottom surface is an adhesive skin-contacting surface that adheres to and conforms to the body surface, a second layer disposed on the top surface of the first layer, wherein the second layer comprises a pad having a plurality of force absorbing zones, and a discontinuity disposed between at least two of the plurality of zones, the first discontinuity comprising a bottom surface and a flexion space between such at least two zones, and wherein flexion of the pad about the first discontinuity does not inhibit motion of the body surface. In a preferred embodiment, there is also an intermediate or carrier layer to hold the padding together upon die cutting. Thus, in some embodiments, the tape comprises more than one layer of pressure sensitive adhesive.

In certain embodiments, the first layer is a layer of adhesive, for example a press-sensitive adhesive, having a sufficient adhesive strength to secure the tape in place during use, but which also allows the tape to be readily removed from the skin after use, preferably in a pain-free manner. In alternative embodiments, the first layer is made of a resiliently stretchable material configured to conform to the surface of the skin, with a bottom surface to which the adhesive is applied, for adhering to the user's skin. Another embodiment is a first layer of pressure sensitive adhesive optimally designed to work adjacent to the skin, a second layer adjacent to the first layer and the padding layer optimally designed to retain the force absorbing padding. A third stretchable material may also be placed between the adhesive layers so as to allow easier manufacturability in cutting and converting the final tape in production. A releasable, protective paper liner may be disposed on the adhesive prior to use. Another material, preferably stretchable, may also be placed between the force absorbing zones and on the outer surface of the pressure sensitive adhesive in order to eliminate exposed pressure sensitive areas which are prone to collecting debris and inhibiting ease of use.

In certain embodiments, each force-absorbing zone is a discrete, separate element which is individually disposed on the first layer, preferably on the top surface of the first layer. Each force-absorbing zone has a base with side walls extending therefrom. The base is secured to the top surface of the first layer such that the flexion surface is located between side walls of adjacent force-absorbing zones, and the bottom surface of the first discontinuity is provided by the top surface of the first layer. In embodiments in which the first layer is a layer of adhesive, each force absorbing-zone is separately bonded to the top surface of the adhesive layer. In those embodiments in which the first layer is a conformable material, each force-absorbing zone is separately bonded to the top surface of this material by the provision of an adhesive between the adjoining surfaces.

In certain embodiments, the bottom surface of the first discontinuity is disposed above the top surface of the first layer. This can be achieved in certain implementations by the segmentation of a single piece of force absorbing material. Segmentation creates a plurality of force absorbing zones which project from the bottom surface of the second layer (i.e. the surface that is disposed adjacent to the top surface of the first layer). Each force absorbing zone has a height. Unitary extensions, which extend between adjacent force absorbing zones, have a height that is less than the height of the force absorbing zones. The projecting plurality of zones may be configured as a pattern.

In certain embodiments, the height of the unitary extension is one-third ($\frac{1}{3}^{rd}$) the height of the adjacent force absorbing zones between which it extends.

In certain embodiments, the height of the unitary extension is about two-thirds ($\frac{2}{3}^{rds}$) the height of the adjacent force absorbing zones between which it extends or between about $\frac{1}{3}^{rd}$ and about $\frac{2}{3}^{rds}$ of the height of such zones.

In certain embodiments, segmentation is achieved by the removal of material from the top surface of the second layer.

Material is removed to create the desired shape, size and pattern of the force absorbing zones and the desired height of the unitary extensions between adjacent force absorbing zones.

In alternative embodiments, segmentation is achieved by the use of a mold into which a moldable, force absorbing material is poured. This enables the creation of the desired shape, size and pattern of the force absorbing zones and the desired height of the unitary extensions between adjacent force absorbing zones.

Various shapes of force absorbing zones can be utilized as required to provide appropriate support to the user's body area. Example shapes include, but are not limited to, a circle, an oval, a square, a rectangle, a diamond, a hexagon or a rounded-hexagon, flowers, chain mail, logos, team mascots etc. A mixture of shapes can be utilized, and a plurality of shapes may be configured in a pattern. In certain embodiments, the side walls of the force absorbing zones have complimentary shapes (e.g., opposing flat walls, opposing convex/concave pairings) that abut across the flexion space when the plurality of force absorbing zones articulate about the first discontinuity.

As described herein, the disposable tape comprises a sheet of adhesive with padding. It will be appreciated that the tape can be wound in overlapping relationship upon itself to form a convolutely wound roll of tape. Also contemplated is a sheet of tape comprising an adhesive layer, a pad having a plurality of force absorbing zones, and a discontinuity, wherein the sheet of tape can have a functional and/or ornamental shape. In an embodiment, when partially unrolled or unfurled from the dispenser in which it is housed, the tape has a length which is defined by the two opposing longitudinal edges and a width which is defined by the distance between opposing longitudinal edges. The tape can be provided in different widths and different lengths, as appropriate to support the user's body area. Non-limiting examples of suitable widths of tape are about 2", 3", 4", 5" or 6". In certain embodiments, at least two force absorbing zones are provided between the opposing longitudinal edges. In alternative embodiments, at least four force absorbing zones are provided between the opposing longitudinal edges. In other embodiments, many force absorbing zones are use, e.g., more than four (4), more than eight (8), more than twelve (12) or more than twenty (20).

It may be advantageous for a tape to be provided with a mixture of force absorbing zones that are capable of absorbing and dissipating energy, such as an impacting force, by differing amounts to provide more particularly tailored support. In certain embodiments, there are at least two sets of the force absorbing zones provided on the tape. Each set is configured to compress by a different height extent under the same impaction force. This can be achieved by providing a first set of force absorbing zones which have a different surface area than the surface area of the force absorbing zones in the second set. In some implementations, the force absorbing zones of the first set have a different height than the height of the plurality of force absorbing zones of the second set. The set with a greater height preferably compresses to a different position than the set with the smaller height, so it is still higher but is compressed more. Alternatively, or additionally, each set is configured to compress by a different height extent under the same impaction force by providing first and second sets of force absorbing zones in which the compressive strength of the zones in the first set is different from the compressive strength of the zones in the second set. There is a balance to be made between the ability of a force absorbing zone to absorb and dissipate an impacting force with considerations such as the conformability of the force absorbing zones, and the overall comfort and appearance of the tape. The use of a mixture of force absorbing zones that compress to differing height extents can help to achieve this balance. For example, if the pad is being used as a knee protector, it may be desirable for the force absorbing zones which cover the knee cap to compress to a lesser height extent than the surrounding force absorbing zones. This improves the comfort when the user is kneeling, because the force absorbing zones will not compress to such an extent that the user will be able to feel the floor underneath.

In certain embodiments, a first set of force absorbing zones have a greater capability of absorbing and dissipating energy than the force absorbing zones of a second set. In certain embodiments, the first set is provided at or near the longitudinal edges of the tape, thereby forming two opposing outer margins of force absorbing zones. A second set is provided within an inner margin of the rolled tape. This provides a tape having outer margins which contain force absorbing zones capable of absorbing and dissipating more energy than the inner margin. It is however envisaged that various uniform or non-uniform patterns of the first set and second set of force absorbing zones can be provided on the tape.

In certain embodiments, a first set of force absorbing zones are made of a material having a greater compressive strength than the compressive strength of material from which the force absorbing zones of a second set of force absorbing zones. In certain embodiments, the first set is provided at or near the longitudinal edges of the tape to form two opposing outer margins and the second set is provided within an inner margin. This provides a tape having outer margins, which contain force absorbing zones capable of absorbing and dissipating more energy than the inner margin. It is however envisaged that various uniform or non-uniform patterns of the first set and second set of force absorbing zones can be provided on the tape.

The compressive strength of the force absorbing zone can be modified by utilizing at least two materials having different compressive strengths. Each force absorbing zone can be a composite of materials. The composite can be generated by the layering of materials having different compressive strengths. For example, the force absorbing zone can have a first material layer and second material layer, the compressive strength of the first material layer being greater than the compressive strength of a second material layer. Specifically, the force absorbing zone is oriented such that the first material layer is positioned nearer to the body than the second material layer, thereby providing a tape in which the material nearer to the body surface has greater force-absorbing characteristics.

In certain embodiments, the tape is provided with a plurality of force absorbing zones all being of the same shape. In certain embodiments, different shapes are utilized for the plurality of force absorbing zones.

Suitable materials from which the force-absorbing zones can be made are readily known to the person skilled in the art. Examples include open-cell and closed-cell foams, such as polyurethane foam, neoprene, rubber, polyvinyl chloride, polyethylene (PE), cross-linked polyethylene, silicone foam, ethyl vinyl acetate (EVA) foam, microcell, and polystyrene foam. In a preferred embodiment, the foam is ethyl vinyl acetate (EVA), a PE-EVA blend, or combinations thereof.

In certain embodiments, each force absorbing zone is a composite of foam layers. The composite comprises at least two layers of foam material, with the material of each layer having a different compressive strength. In certain embodiments, each force absorbing zone has a first foam layer which has a greater compressive strength than the second foam layer, and the force absorbing zone is orientated such that the first foam layer is nearer to the body surface, when applied. Different compressive strength can be achieved by the use of foam materials having different densities.

In certain embodiments, the second layer of the tape comprises a plurality of interconnected fluid or gel-filled sacs. Specifically, the second layer of the tape comprises air-filled sacs.

An advantage of the tape as described herein, is that is allows the user to tailor the amount of the tape being applied to any particular body part. The user can cut a required length of tape using scissors. The user may simply cut the tape in a straight line from opposing perimeter edges. However, depending on the pattern of force-absorbing zones, this may require the user to cut through a force-absorbing zone, the ease of which is dependent on the thickness of the pad. Advantageously, in certain embodiments a tear line, for example, a line of perforations, is provided along the flexion space. This allows the user to simply dispense the required length of tape by tearing along the tear line.

In further certain embodiments, a third layer is disposed on the second layer such that the second layer is sandwiched between the first and second layer. In certain embodiments, the third layer completely encloses the second layer, such that the force absorbing zones are not visible. In such embodiments, the third layer is made of a resiliently stretchable material which stretches in response to flexion of the second layer. Suitable materials, for example, include materials made of polyester or elastane fibers, for example Lycra®. Such a Lycra layer may be put formed flat fully on the top surface of the padding material, or alternatively, it could be formed around each individual padding sections so as to accentuate the look of the padding material and perhaps take advantage of the PSA potentially still resident around each of the padding sections. In alternative embodiments, the third layer is localized on the top surface of the force absorbing zones. In such embodiments, the third layer is a thin layer of plastic or a skinning foam. The provision of a third layer can increase the durability of the tape and minimizes the disintegration of the force-absorbing zones during use. If the tape is going to be used on areas of the body which are not covered by clothing, then it may be desirable to provide the third layer in different colors, for example "team" colors. Advantageously, in embodiments in which the tape includes a third layer which completely encloses the second layer, the third layer includes a tear line which is coincident with a tear line in the second layer. Furthermore, in embodiments in which the first layer is a resiliently stretchable material, a tear line which is coincident with the tear lines provided within in the second layer and third layer is provided.

In use, it may be desirable for the tape to be secured not only to the skin, but also to any overlying clothing. Advantageously therefore, the upper surface of the tape is provided with a means of securing the tape to overlying clothing or other protective devices. For example, the upper surface of the tape is provided with pressure-sensitive adhesive, or Velcro.

BRIEF DESCRIPTION OF THE DRAWINGS

The foregoing and other objects and advantages will be appreciated more fully from the following further description with reference to the accompanying drawings. The depicted embodiments are to be understood to as illustrative and not limiting in any way.

FIG. 1 is a cross-sectional view of an illustrative tape in which individual foam pieces are adhered to a layer of adhesive to form a pattern of adjacent force-absorbing zones with flexion spaces provided in between.

FIG. 2 is a cross-sectional view of an illustrative tape in which a unitary piece of foam is adhered to a layer of adhesive, and the foam is segmented to form a pattern of adjacent force-absorbing zones with flexion spaces provided in between.

DETAILED DESCRIPTION OF CERTAIN INVENTIVE EMBODIMENTS

Embodiments of this application relate to a disposable padded tape for use in protecting against injury. To provide an overall understanding of the devices and methods described herein, certain illustrative embodiments will be described. In the discussion below, the tape can be configured as a sheet. Optionally, the tape can be rolled. When unrolled/unfurled from its packaging, the tape has a length defined by opposing longitudinal edges and a width extending between these longitudinal edges. Where a surface is described to say a "skin-contacting surface" or "body-contacting surface" it is assumed to also mean contacting any equipment, padding, protective wear such as shin guards, elbow pads, wrist guards, and ankle supports, athletic tape such as cohesive tape, trainer tape, kinesiology tape, and spatting tape, bandages, wraps, gauze, clothing, footwear or any other appropriate surface that can come into contact with a body surface. Also contemplated within the meaning of "skin-contacting surface" or "body-contacting surface" is the exterior surface of a mammal. For example, the tape can be applied to horse forelocks to protect against injury. Additionally, the tape can be applied to the surface of a mammal to protect the skin against chafing from equipment such as a saddle.

Figure 1:
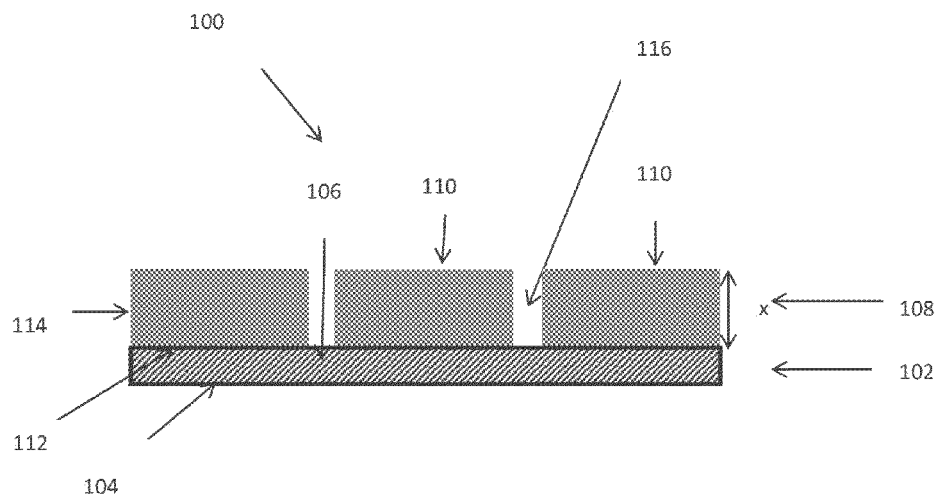

FIG. 1 illustrates a cross sectional view of an illustrative tape 100. The tape consists of a biocompatible first layer 102 of pressure-sensitive adhesive (PSA), urethane, polyurethane, or hydrogel which has a bottom surface 104 that functions, in use, as the skin-contacting surface, and a top surface 106. As used herein, PSA refers to an adhesive which forms a bond when pressure is applied to marry the adhesive with the adherend. Preferably, the PSA provides adhesion upon application of a light pressure and removability from the surface to which the PSA is applied through a light pulling force. PSAs include an elastomer compounded with a suitable tackifier such as, for example, a resin ester. The elastomer can be a rubber, acrylate, silicone, polyurethane, polyester, polyether, or combinations thereof. Suitable elastomers include, without limitation, acrylics, butyl rubber, ethylene-vinyl acetate, natural rubber, nitriles, silicone rubbers, styrene block copolymers, styrene-butadiene-styrene, styrene-ethylene/butylene-styrene, styrene-ethylene/propylene, styrene-isoprene-styrene, and vinyl ethers. Suitable PSAs are compatible to skin, possess robust skin adhesion qualities, are breathable to air and moisture, and allow for removal without skin trauma. Thus, PSAs are selected based upon their ability to adhere to a body surface and resistance to moisture and skin variations such as oiliness or dryness. Useful acrylic based PSAs include, but are not limited to, those taught in U.S. Pat. No. 5,947,917 (Carte), and U.S. Pat. No. 5,164,444 (Bernard, describing an acrylic emulsion), U.S. Pat. No. 5,623,011 (Bernard, describing a tackied acrylic emulsion). It can also be a curable mixture of monomers with initiators and other ingredients such as those taught in U.S. Pat. No. 5,232,958 (Ang, describing UV cured acrylic) and U.S. Pat. No. 5,232,958 (Mallya et al, detailing EB cured). The disclosures of these patents and the pending application as they relate to acrylic adhesives are hereby incorporated by reference. As used herein, PSAs relate to specific pressure sensitive adhesives as described above and also include adhesive urethanes and hydrogels as described below. Thus, in some embodiments, the first layer 102 is constructed using a skin-like urethane as the base structure. For example, the urethane can be a breathable polyurethane material such as 3M's Tegaderm™ transparent dressing, 3M 9833, or 3M 9844 (Minnesota Mining and Manufacturing Company, St. Paul, Minn.) or a polyurethane-based film such as the pressure sensitive adhesives available from DermaMed® (DermaMed Coatings Company, Tallmage, Ohio). In still other aspects, the first layer 102 is constructed of an adhesive hydrogel. The hydrogel can be an electrically conductive adhesive hydrogel such as the hydrogel described in U.S. Pat. No. 5,800,685 to Perrault et al. Advantageously, the first layer 102 comprising an adhesive provides a skin contouring adhesion, transparency, and breathability.

The PSA layer is configured to adhere to a body surface independently of the exterior temperature, humidity levels, and individual's skin type. For example, the PSA can adhere to oily, normal, and dry skin. Thus, in preferred embodiments, the first layer is substantially sweatproof and maintains adhesion against a body surface during exercise and perspiration. In a particularly preferred embodiment, the PSA is substantially waterproof. Optionally, the first layer 102 can further include a feedback indicator. The feedback indicator interacts with the wearer and the tape and provides information relative to the interaction such as the sodium chloride content in sweat, the temperature of the skin, pH, and/or impact force absorbed by the tape. The feedback indicator can be embedded in the adhesive layer, or layered on the body contacting surface of the first layer. The feedback indicator can be a chemical marker, an electrical feedback element, or combinations thereof. For the chemical marker, indications of sodium chloride content, skin temperature, pH, etc. can be evident by the change in coloration of the tape. For example, the feedback indicator can include a thermosensitive color sensitive layer, whereby heat from the body contacting side of the first layer activates the thermosensitive color layer to produce a color reflective of the skin surface temperature of the wearer. Other tactile surface pressure sensors and/or force sensors may likewise be included to capture the pressure profile such as the sensors made by Sensor Expert (Sensor Products Inc., Madison, N.J.). Advantageously, the pressure indicating sensor is configured to reveal the distribution and magnitude of pressure. Another non-limiting example of a pressure indicating sensor may include FujiFilm PreScale® pressure sensitive indicator film. In certain aspects, the first layer 102 includes an electrical feedback element. The electrical feedback element can be constructed from a conductive additive incorporated into the adhesive to detect, for example, electromyography (EMG) signals from the muscle area underneath the tape assembly. Thus, the tape can be used as a protective element (as described in greater detail below) and also as an indicator of muscle activity around the protected area. In still another aspect, the tape can optionally include a conductive element in communication with the first layer of the tape and an electrical device configured to send currents through small electrodes that target muscles. Suitable devices may include, for example, an E-stim device or a neuromuscular electrical stimulation (nmes) device to electrically stimulate nerve fibers to alleviate or block pain or to activate muscle fibers.

The PSA can optionally include an antimicrobial layer to improve comfort and reduce the growth of microbes. The top surface 106 of the first layer 102 comprises a carrier layer. The carrier can be a woven or non-woven fabric. In preferred embodiments, the carrier is a two-way stretch non-woven material. In a particularly preferred embodiment, the liner is a four-way stretch non-woven material.

Disposed on the top surface of the first layer is a second layer 108 having a pattern of shaped pieces of foam 110, for example, cube-shaped pieces. The foam serves to absorb and dissipate energy. Each foam piece has a base 112 and side walls 114 extending upwards to give each foam piece a height x. Each individual foam piece is adhered to the surface 106 along its respective base using an adherend such as a PSA. The foam pieces form force-absorbing zones of the second layer. In between the pieces of foam are flexion spaces 116, the bottoms of which are formed by the surface 106. The flexion spaces and the bottom surfaces between two zones provide a discontinuity between those zones. Flex is achieved by introducing discontinuities in the sheets of foam and ensuring carriers and PSAs do not inhibit stretch. Any foam piece can flex about the discontinuity without inhibiting motion of the body part being wrapped or protected. In some implementations, adjacent force-absorbing zones or foam pieces flex about the bottom surface of the discontinuity, flexing toward each other or away from each other. During such flexion, the upper areas of adjacent zones or foam pieces may touch, which allows the adjacent zones to move relative to each other so as to additionally absorb an applied force.

The physical characteristics of some or all of the foam pieces can be modified as discussed below to provide foam pieces which are configured to compress to different heights under the same impaction force. Although not shown, adhesive can be provided on the top surface of the second layer, allowing the top of the second layer to adhere to overlying clothing or other protective devices. The adhesive on both the bottom surface of the first layer, and if present, on the top surface of the second layer can optionally be covered with a protective paper liner prior to use. In a particularly preferred embodiment, the tape comprises a release liner, an adherend such as PSA adjacent to the skin, a carrier layer, and a padding layer. The carrier layer can be a non-woven fabric or a thin plastic film. Advantageously, a PSA holds the pad to the carrier layer. The PSA can be the same PSA used in the first layer. Alternatively, the PSA can be a relatively stronger adhesive which secures the force absorbing zones to the top surface of the first layer.

Figure 2:
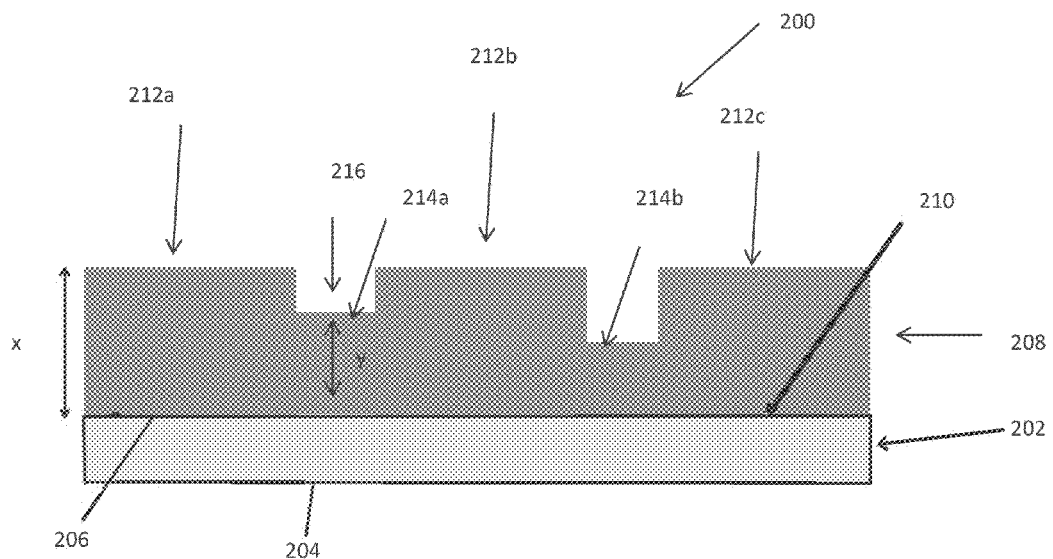

FIG. 2 illustrates a cross-sectional view of an illustrative tape 200. The tape includes a first layer 202 of pressure-sensitive adhesive (PSA) with a bottom surface 204 that functions, in use, as the skin-contacting surface, and a top surface 206. Disposed on the top surface of the first layer is a second layer 208 structured as a unitary piece of foam. This piece of foam has a bottom surface 210 which is adhered to surface 206 with a pressure sensitive adhesive. The PSA can be rubber based or acrylic based. In preferred embodiments, the PSA is acrylic based. The foam is segmented to produce a pattern of foam sections (212a, 212b, 212c) which extend upwardly from surface 210, each having a height x, and which function as the force absorbing zones. As illustrated, a unitary extension 214a spans between and connects force absorbing zones 212a and 212b, whereas unitary extension 214b spans between and connects force absorbing zones 212b and 212c. The top surface of the unitary extensions forms the bottom of the flexion space 216 between adjacent force absorbing zones. The area of flexion space between adjacent force absorbing zones can be altered by altering the height y of the unitary extensions. For example, unitary extension 214a has a height y which is about ⅔ of x. In comparison, the height y of unitary extension 214b is about ½ of x. Although not shown, adhesive can be provided on the top surface of the second layer (e.g., on top of the force absorbing zones) to allow the top of the second layer to adhere to overlying clothing or other protective devices. The adhesive on both the bottom surface of the first layer and if present, on the top surface of the second layer is preferably covered with a protective paper liner prior to use.

In certain embodiments, the force absorbing zones of the second layer can be configured to compress to different heights under the same impaction force. FIGS. 3A-3D illustrate cross-sectional views of illustrative embodiments of tapes 300; 400; 500; 600 which comprise a first layer 302; 402; 502; 602 of pressure-sensitive adhesive and a second layer 304; 404; 504; 604 structured as individual pieces of foam, which function as the force absorbing zones. However, some of the illustrative embodiments discussed below are also suitable for use in tapes which are manufactured utilizing a unitary piece of foam.

Figure 3A:
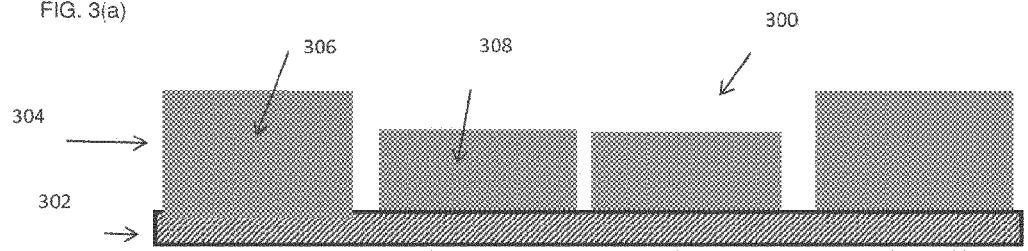
FIGS. 3A-D are cross-sectional views of illustrative tape provided with force-absorbing zones having different force-absorbing capabilities due to varying physical characteristics.

In FIG. 3A, the second layer 304 consists of two sets (306; 308) of foam pieces which are made of the same type of foam, but differ in height. The pieces of foam of the first set have a greater height than the pieces of foam of the second set. A piece of foam from the first set 306 is distributed near each of the opposing longitudinal edges of the tape to form opposing outer margins. Two pieces of foam from the second set 308 are distributed within the margin of the tape. When a force is applied the two different zone sets compress differently (e.g., one compresses more than the other); thereby providing differential and customizable support for a person's body part.

Figure 3B:
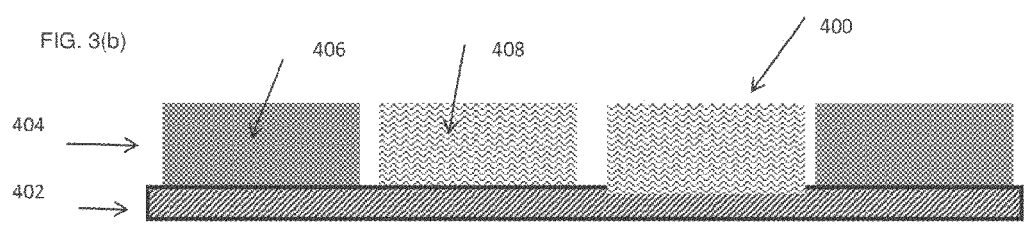

In FIG. 3B the second layer consists of two sets (406; 408) of foam pieces which are made of different types of foam, having the same height. Suitable foams include, without limitation, ethyl vinyl acetate (EVA), a closed cell polyethylene (PE), neoprene, rubber, and/or a PE-EVA blend. The pieces of foam of the first set have a greater compressive strength than the pieces of foam of the second set. A piece of foam from the first set 406 is distributed near each of the opposing longitudinal edges of the tape to form opposing outer regions. Two pieces of foam from the second set 408 are distributed within the inner margin of the tape. This structure can be advantageous in situations in which the impacting force is not received in a direction which is perpendicular to the skin but is received at an oblique angle.

Figure 3C:
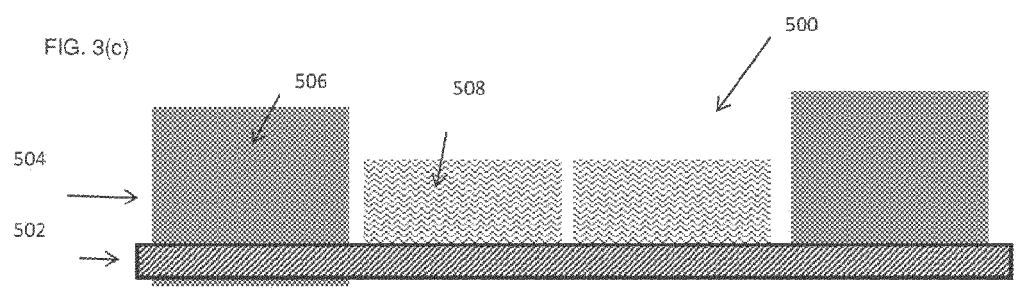

In FIG. 3C the second layer consists of two sets (506; 508) of foam pieces which are made of the different types of foam, and also have different heights. The pieces of foam of the first set have a greater compressive strength and a greater height than the pieces of foam of the second set. A piece of foam from the first set 506 is distributed near each of the opposing longitudinal edges of the tape to form opposing outer regions. Two pieces of foam from the second set 508 are distributed within the inner margin.

Figure 3D:
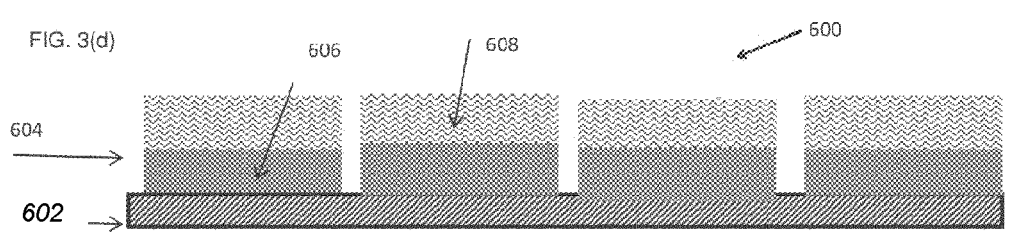

In FIG. 3D the second layer 604 consists of two sets (606; 608) of foam pieces in which the first set 606 and the second set 608 are made of a composite of two types of foam. Advantageously, the first foam and the second foam have a compression set to absorb and dissipate energy. In one embodiment, the first foam has a greater compression set than the second foam. In another embodiment, the compression set of the second foam exceeds the compression set of the first foam. As illustrated, the second layer 604 consists of a first type of foam 606 having a high compressive strength which is provided nearest to the first layer 602 of the tape. Layered upon this, is a second type of foam 608 which has a lesser compressive strength. Whilst the provision of a hard, more compressive foam adjacent to the skin ensures that the padded tape is capable of absorbing impaction forces and thus protecting the individual from any impact trauma, the softer, less compressive foam on the outer surface of the tape enhances the wearability of the tape, due for example to the greater conformability of the softer foam. For example, if the tape is being worn to protect the knee, the softer foam enhances the comfort of the pad, when the person is kneeling on a hard surface as the softer foam conforms to the surface to a greater degree than would a stiff foam.

Figure 4A:
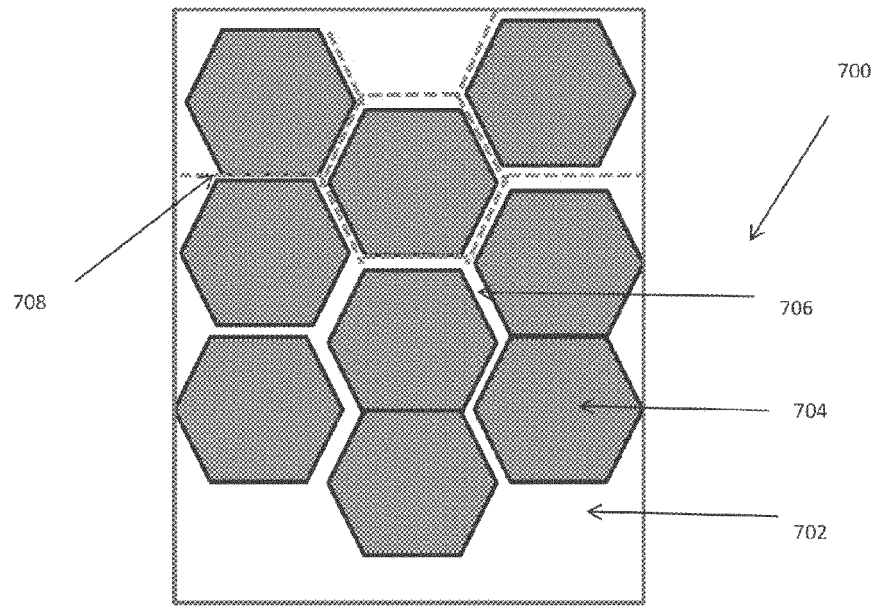
FIGS. 4A and 4B are plan views of an illustrative tape having varying spacing of hexagonal force absorbing zones.
Figure 4B:
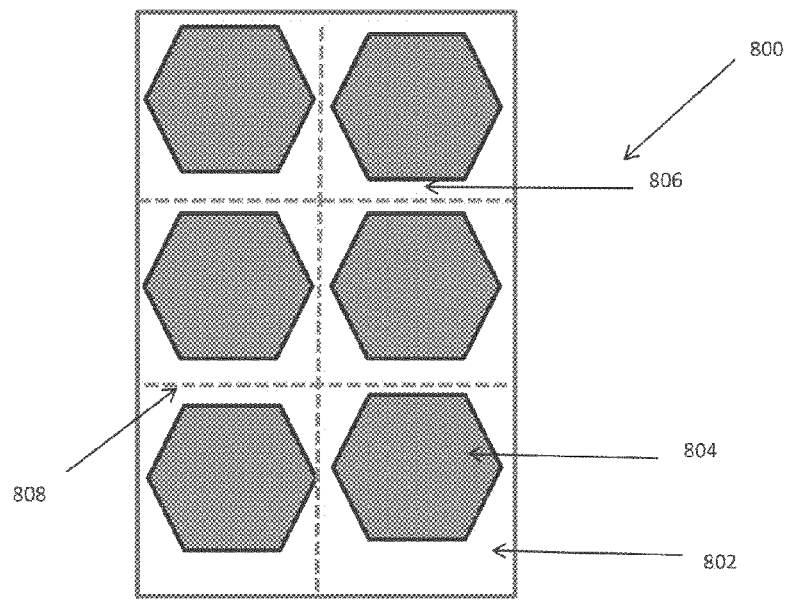

As shown in plan view, the illustrative tapes 700; 800 in FIGS. 4A and 4B, are formed with a second layer 702; 802 in which hexagonal force absorbing zones 704; 804 are distributed in varying patterns. A user can select the desired patterns. The pattern selected is governed by the amount of flexion space (706; 806) desired between adjacent zones. Tear lines (708; 808) formed from perforations can be provided within the tape, in certain embodiments disposed between adjacent flexion zones, and allow the user to tear off the desired amount of tape without having to tear through a force absorbing zone. In some embodiments, tear lines are not provided; however, depending on the composition of at least the first layer, the tape can still be torn without severing a force absorbing zone. In still other embodiments, a user can employ scissors, shears, tape cutters, or other suitable cutting means to select the amount of tape desired from a sheet or roll.

Figure 5A:
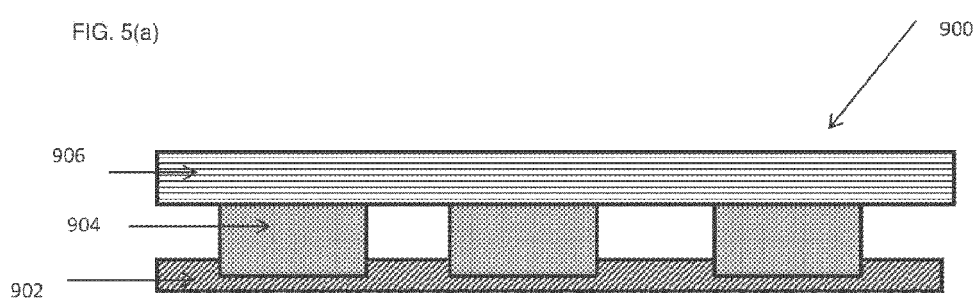
FIGS. 5A and 5B are cross-sectional views of an illustrative tape having a protective layer disposed on the top surface of the force absorbing zones.
Figure 5B:
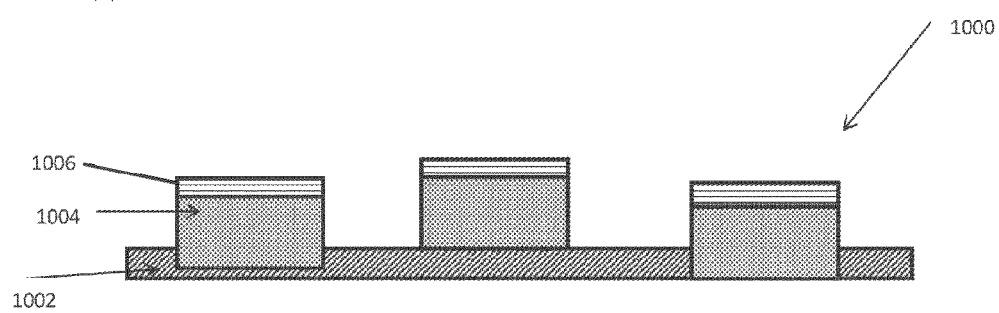

FIGS. 5A and 5B illustrate further illustrative tape embodiments (900; 1000) in which a protective third layer, is applied to the top surface of the second layer. The illustrated tapes can be formed according to any of the embodiments disclosed herein, for example, in any of FIGS. 1-4(b). As illustrated in FIG. 5A, the tape 900 is provided with a first layer 902, a second layer 904 and third layer 906, with the third layer being co-planar with the first layer and extending between the longitudinal edges of the tape. The third layer is a resiliently stretchable material, for example Lycra®. Alternatively, as shown in FIG. 5B, discrete islands of material can be localized onto the top surface of the force absorbing zones 1004 to form a third layer 1006, which protects the force absorbing zones but still maintains separation between the tops of adjacent zones. One example of a suitable material is a skinning foam. Although not shown, adhesive can be provided on the top surface of the third layer. The adhesive on both the bottom surface of the first layer, and if present, on the top surface of the third layer is preferably covered with a protective paper liner prior to use. Consistent with the structure illustrated and described in FIG. 5A, FIG. 5B also includes a first layer 1002.

Figure 6A:
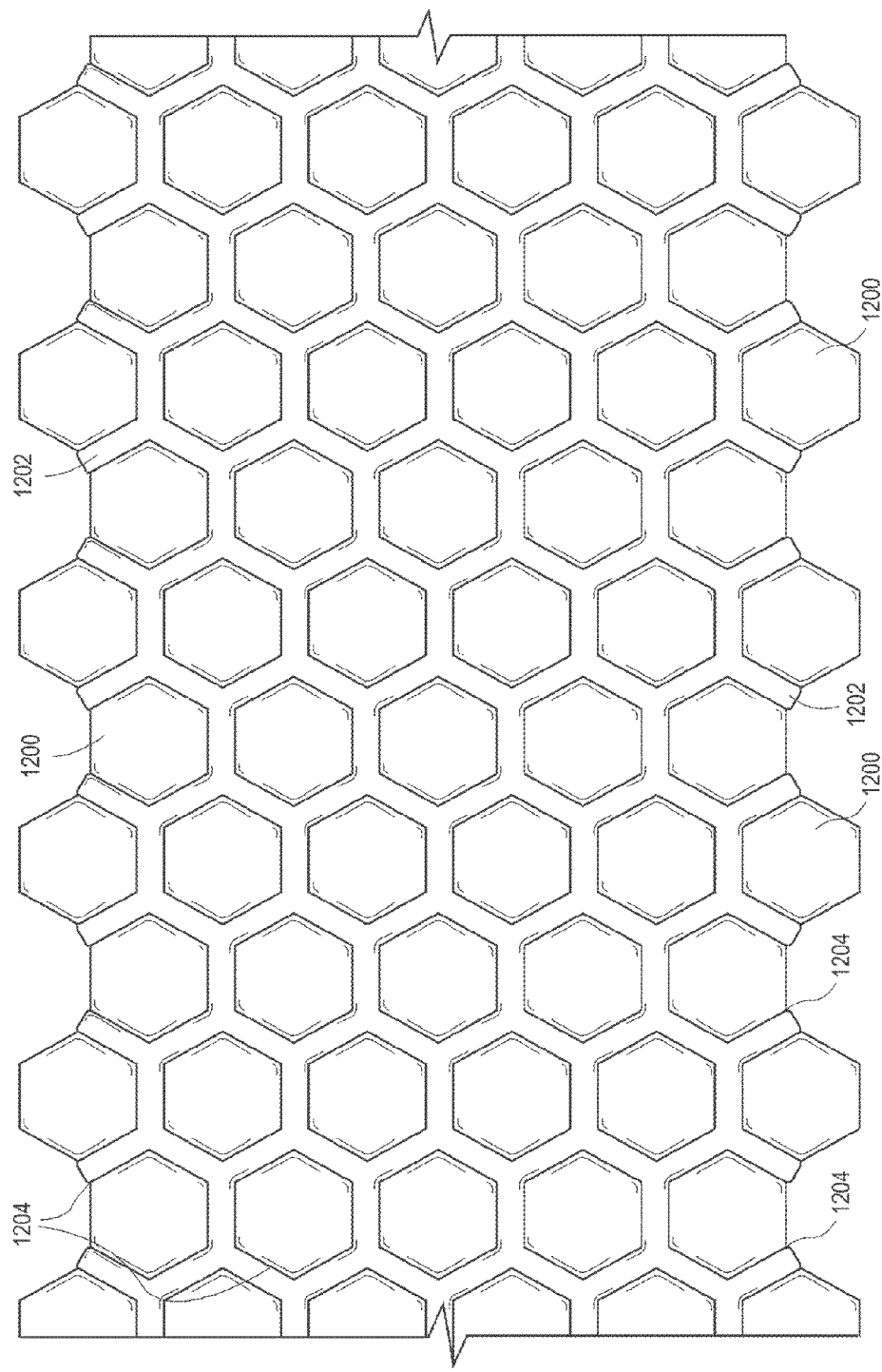
FIG. 6A-6C are plan views of an illustrative tape having force absorbing zones disposed within a foam core.
Figure 6B:
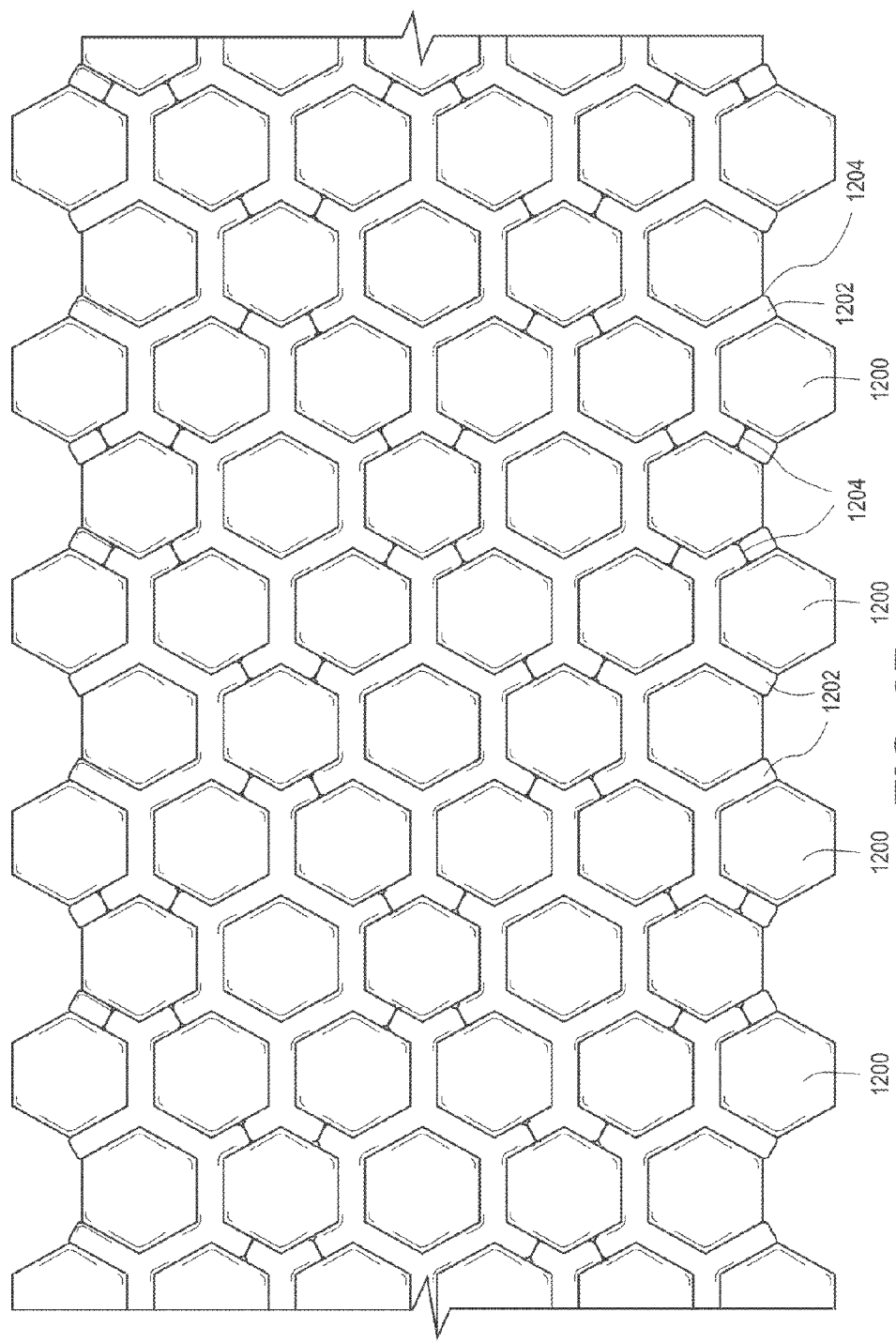
Figure 6C:
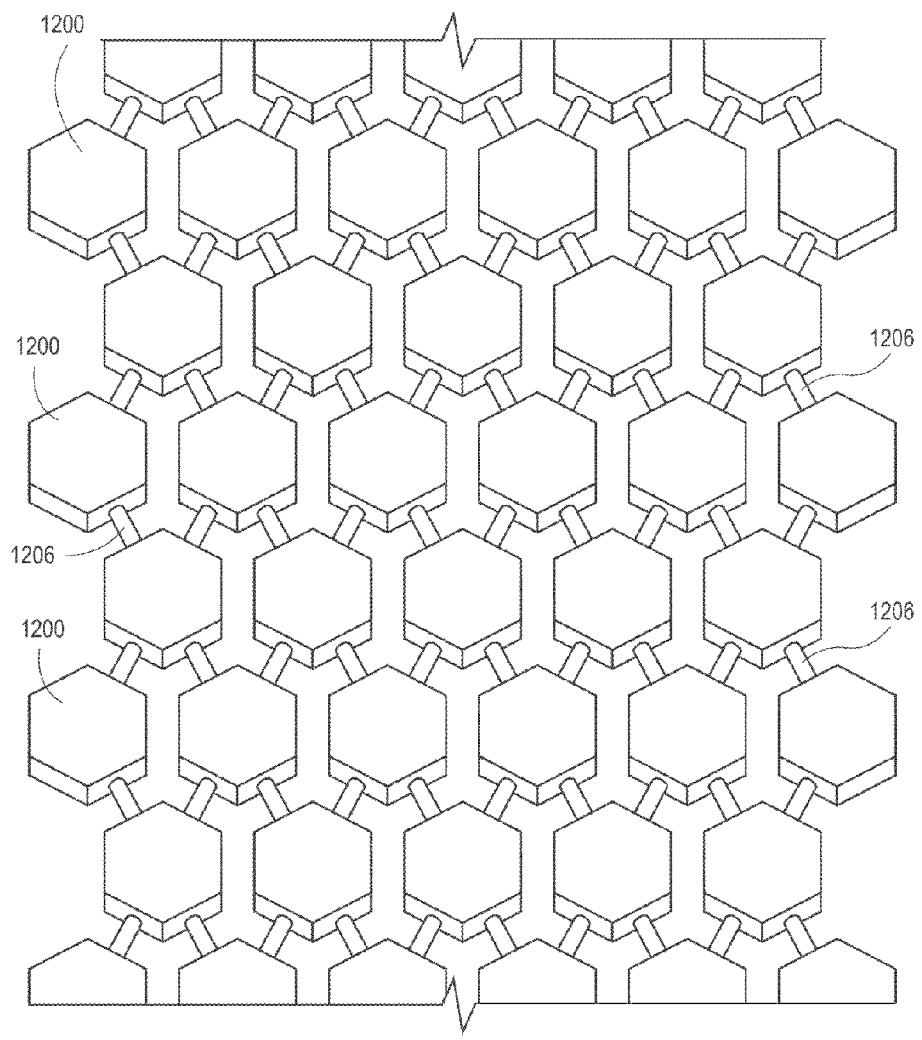

FIGS. 6A-6C illustrate further embodiments of the disposable tape. FIG. 6A is a plan view of a disposable tape, wherein a single sheet of foam is die cut to create a pattern of force absorbing zones 1200 surrounded by a foam core 1202. A single sheet of foam is die cut/segmented to create force absorbing zones 1200 and discontinuities 1204 around the force absorbing zones 1200. The force absorbing zones 1200 are disposed within the foam core 1202, which borders the force absorbing zones 1200. The discontinuity 1204 between the force absorbing zone 1200 and the foam core 1202 allows for movement between flexion space. As illustrated in FIG. 6B, the foam core 1202 can be further segmented to allow for greater movement relative to the discontinuities 1204 and force absorbing zones 1200 as well as for movement between the discontinuities 1204 of the foam core 1202. As illustrated in FIGS. 6A and 6B, the force absorbing zones are configured as hexagons and the foam core has a honeycomb appearance but it will be appreciated by a person of ordinary skill in the art that other shapes can be employed. As FIG. 6B illustrates, additional discontinuities can be formed about the foam core to provide even greater flexion and movement. FIG. 6C is yet another embodiment of the disposable tape, wherein the foam core is articulated such that substantially all of the foam core surrounding the force absorbing zones 1200 is removed except for connectors 1206.

Figure 7:
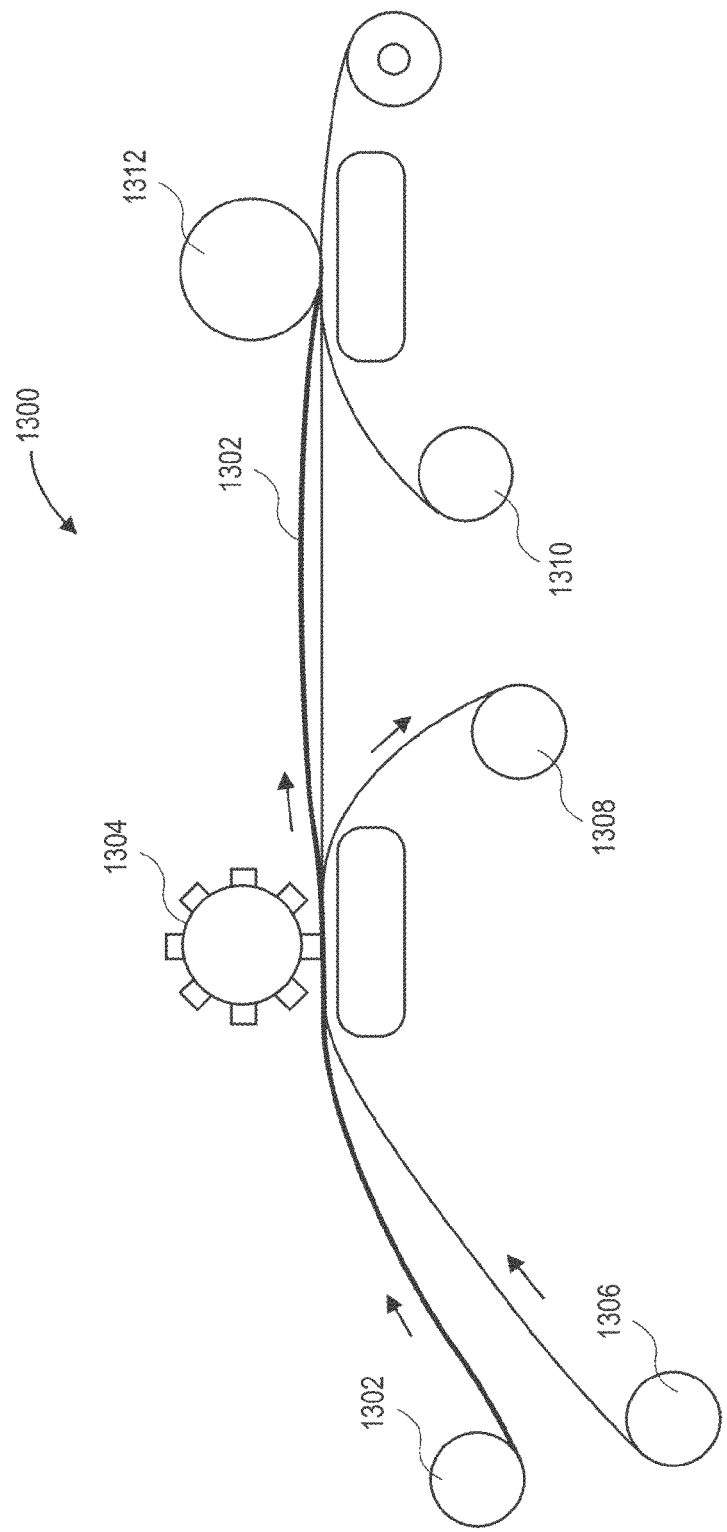
FIG. 7 is a schematic drawing of a manufacturing process for producing disposable tape.

The sheet of disposable tape can be formed by cutting a pattern into a sheet of foam such that discontinuities are formed between the force absorbing zones and the foam core. As illustrated in FIG. 7, during manufacture, a layer of foam 1302 is fed through an assembly 1300 and a cutting means 1304 such as a rotary die cutter cuts the foam layer to create force absorbing zones and discontinuities. The force absorbing zones can be surrounded by a foam core such as the core described with reference to FIGS. 6A and 6B. Optionally, and as illustrated in FIG. 7, a waste liner 1306 comprising an adhesive such as a pressure sensitive adhesive can be co-fed through the assembly prior to passing through the cutting means 1304 such that the foam core is substantially disassociated from the force absorbing zones and adheres to the waste liner 1308, leaving a foam layer having force absorbing zones attached by connectors (as illustrated and described with reference to FIG. 6C). The die cut foam layer travels on the assembly and a first layer 1310 having an adhesive such as a PSA and a liner is married to the foam layer comprising the force absorbing zones and discontinuities between the force absorbing zones and the connectors. Marriage of the first layer to the second layer is accomplished by the application of pressure. As illustrated, a rotary press 1312 can be employed.

A kit for protecting a body surface from injury or pain is also provided. The kit includes disposable tape as described herein and additional double sided adhesive such as a double sided PSA. The tape can be applied and then removed. The paper liner can be reapplied until subsequent use and double sided adhesive is used to maintain an adhesion to the body surface upon subsequent use. The kit can include a pre-application wipe such as a moist towelette, cleansing wipe, or alcohol wipe to reduce the amount of dirt, dead skin cells, and/or oil to promote a better surface for adherence of the tape to the body/skin surface. Alternatively or additionally, the kit can include a powder, lotion, or spray to prepare the skin surface prior to adhesion to the tape.

The tape can be used during physical activities such as sporting activities to protect the body of a wearer. Thus, another feature of the invention is a method of protecting an individual from injury. As used herein, protecting an individual from injury includes protection against incurring injury during activity as well as protection of previous injuries from re-injury during continued activity. Protection is accomplished particularly with regard to athletic activity in certain embodiments. However, the tape can be used in any field where reduction of friction, chaffing, and impact injuries are desirable. The method includes applying tape as described herein to the body surface of the individual, wherein the tape serves to absorb force and prevent injury, minimize chafing, and/or reduce irritation. The tape can be positioned directly on the surface of the skin of an individual.

Figure 8:
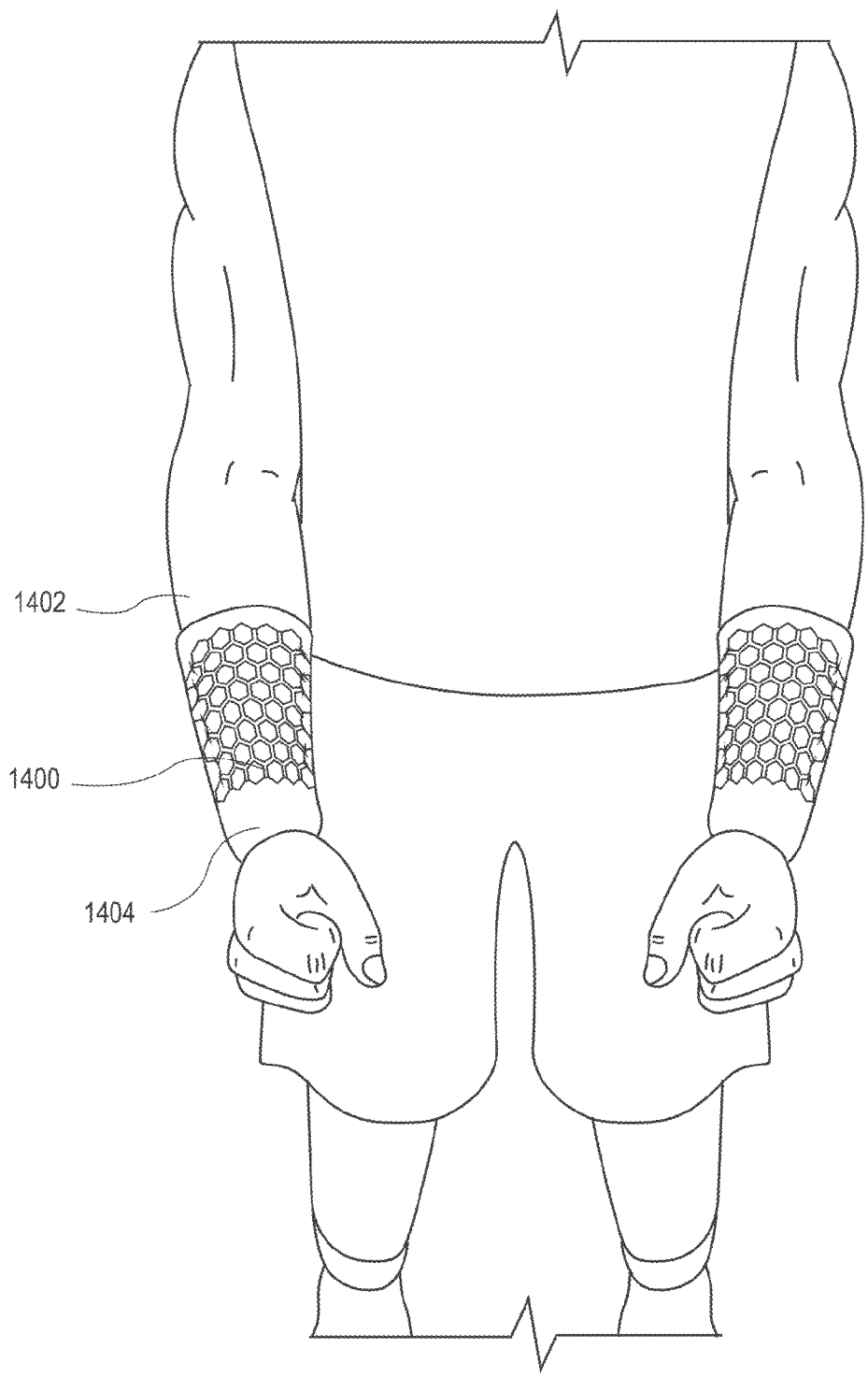
FIG. 8 is a perspective view of one embodiment of disposable tape applied about the forearm of an individual.

Alternatively or additionally, the tape can be applied over clothing, tape, bandages, padding, support braces, protective wear, casts, or footwear. FIG. 8 is a perspective view of one embodiment of disposable tape 1400 applied about the forearm 1402 of an individual. As illustrated in FIG. 8, the tape 1400 can be applied over conventional athletic tape 1404 for added support and protection against injury. The tape can likewise be applied directly to the surface of equipment to reduce irritation or injury to a body surface. For example, the tape as described herein can be applied to athletic equipment such as, in the case of a football player on the surface of the player's padding to prevent skin irritation and provide additional force absorption. As will be appreciated by a person of skill in the art, the tape can likewise be applied over a bandage or athletic tape rather than directly to an individual's skin surface to prevent against further injury.

Figure 9:
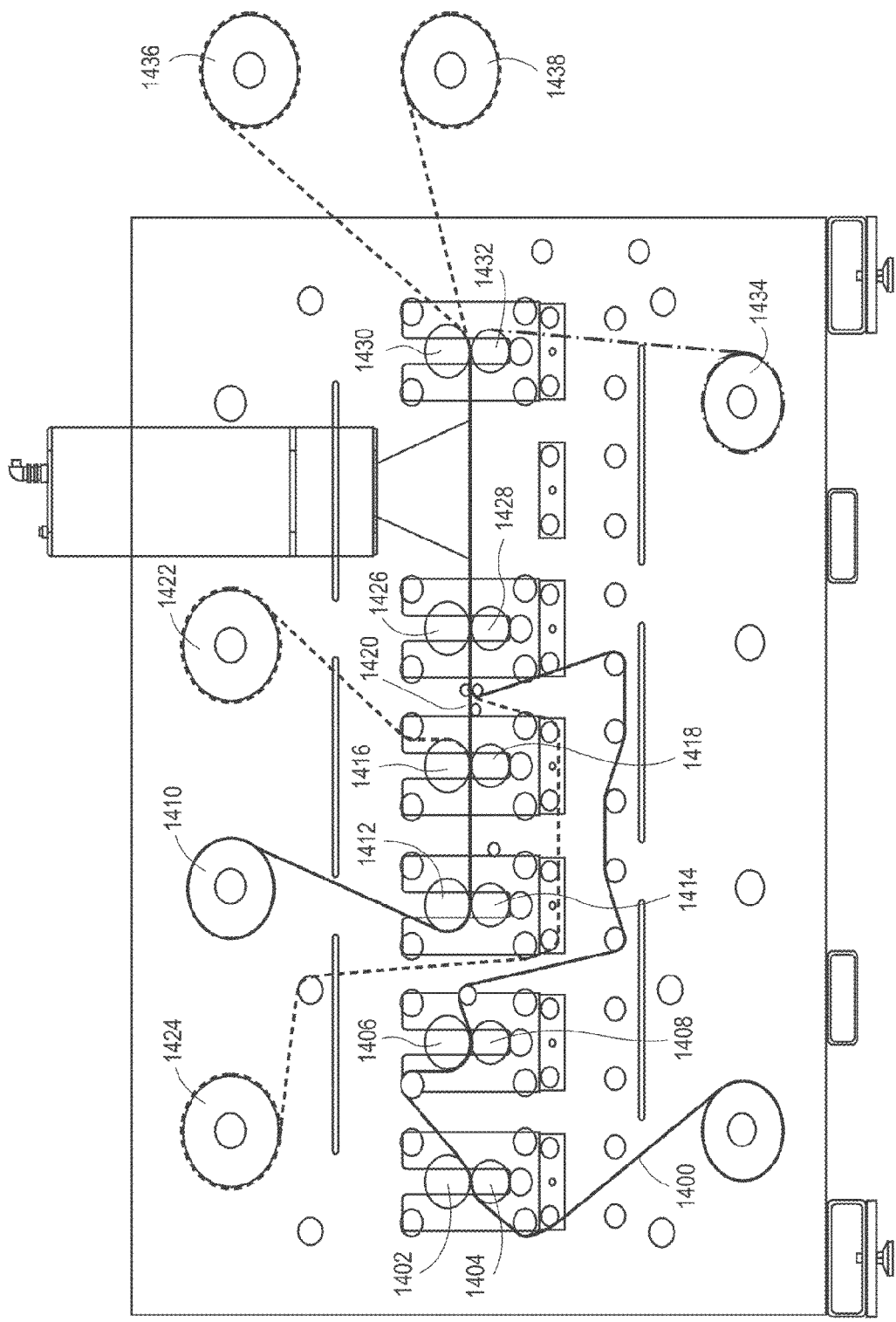
FIG. 9 is a schematic drawing of a manufacturing process for producing disposable tape.

FIG. 9 illustrates another aspect of the manufacturing process for aspects of the disposable tape. The process utilizes a light tack/hard tack processing technique. At step 1 the first layer 1400 is accepted and aligned between the nip 1402 and anvil 1404. As described above, the first layer 1400 can be a polyurethane layer having a pressure sensitive adhesive and a liner. The first layer 1400 is passed through the nip 1402 and anvil 1404 and the pressure applied lightly tacks the components of the first layer 1400. The first layer 1400 is scalloped on its back and sent between the anvil 1406 and a die 1408. Next, the foam layer 1410 is introduced and fed through a nip 1412 and anvil 1414. The foam layer 1410 is then passed through a die 1416 and anvil 1418 and the force absorbing zones are die cut into the foam layer. The strip bar/bullnose assembly 1420 removes and diverts the foam waste matrix 1422 and foam liner waste 1424. The foam layer 1410 is fed through the nip 1426 and anvil 1428 and pressed onto the first layer 1400 having the polyurethane and pressure sensitive adhesive and liner. The pressure applied by the anvil 1428 adheres the first layer 1400 to the foam layer 1410. The first layer 1400 and foam layer 1410 are then aligned and accepted through die cut 1430 and anvil 1432 to trim the edges away. The finished roll 1434 is obtained and the trim waste 1436, 1438 are collected by external rewind.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A kit comprising:
    a disposable tape configured for application to a body contacting surface for the prevention or treatment of an injury to an individual, and a double sided pressure sensitive adhesive, wherein said tape comprising;
        a first continuous layer having a bottom and top surface,
        a second layer disposed on the top surface of the first layer, wherein the second layer comprises a plurality of force absorbing zones, and
        a discontinuity disposed between each of the plurality of force absorbing zones, each discontinuity having a bottom surface and a flexion space between the at least two force absorbing zones; wherein flexing of said force absorbing zones about a first discontinuity allows motion of the body contacting surface;
        a plurality of tear lines formed from perforations in the second layer, wherein said plurality of tear lines are positioned between adjacent force absorbing zones;
    the double-sided pressure sensitive adhesive having a first adhesive side configured to attach to the bottom surface of the first continuous layer and a second adhesive side configured to attach to the body contacting surface;
    wherein said disposable tape is would in overlapping relationship upon itself; and
    instructions for applying said disposable tape to a body contacting surface and reapplying said disposable tape with a portion of said double sided adhesive.

2. The kit of claim 1, wherein said double sided pressure sensitive adhesive further comprises a protective paper removably attached to a surface of the pressure sensitive double-sided adhesive.

3. The kit of claim 2, further comprising instructions for reapplying the protective paper to the surface of the double-sided pressure sensitive adhesive.

4. The kit of claim 1, further comprising a pre-application wipe and instructions for preparing the body contacting surface prior to application of said disposable tape.

5. The kit of claim 4, wherein said pre-application wipe is selected from the group consisting of a moist towelette, a cleansing wipe, and an alcohol wipe.

6. The kit of claim 1, wherein each force absorbing zone has a base with side walls extending therefrom, and wherein the base is secured to the top surface of the first layer and the flexion space is located between side walls of adjacent force absorbing zones.

7. The kit of claim 1, wherein the plurality of force absorbing zones comprise a foam material selected from the group consisting of ethylene vinyl acetate (EVA), polyethylene (PE), or combinations thereof.

* * * * *